US008815569B2

(12) United States Patent
Zelinski et al.

(10) Patent No.: US 8,815,569 B2
(45) Date of Patent: Aug. 26, 2014

(54) METHODS FOR PRESERVING AND/OR STORING CELLS HAVING A NITRILASE OR NITRILE HYDRATASE ACTIVITY

(75) Inventors: Thomas Zelinski, Neuleiningen (DE); Maria Keβeler, Mannheim (DE); Bernhard Hauer, Fußgönheim (DE)

(73) Assignee: BASF SE, Ludwigshafen (DE)

( * ) Notice: Subject to any disclaimer, the term of this patent is extended or adjusted under 35 U.S.C. 154(b) by 1960 days.

(21) Appl. No.: 10/541,427

(22) PCT Filed: Dec. 24, 2003

(86) PCT No.: PCT/EP03/14880
§ 371 (c)(1),
(2), (4) Date: Jul. 5, 2005

(87) PCT Pub. No.: WO2004/063357
PCT Pub. Date: Jul. 29, 2004

(65) Prior Publication Data
US 2006/0110808 A1    May 25, 2006

(30) Foreign Application Priority Data

Jan. 8, 2003 (DE) .................................. 103 00 500

(51) Int. Cl.
*C12N 1/04* (2006.01)
(52) U.S. Cl.
USPC ......... 435/260; 435/136; 435/252.3; 435/243
(58) Field of Classification Search
USPC ............................ 435/260, 136, 252.3, 243
See application file for complete search history.

(56) References Cited

U.S. PATENT DOCUMENTS

| | | | |
|---|---|---|---|
| 3,779,869 A | 12/1973 | Zienty | |
| 3,898,128 A * | 8/1975 | Chibata et al. | 435/109 |
| 4,343,900 A | 8/1982 | Watanabe | |
| 4,526,867 A * | 7/1985 | Chibata et al. | 435/178 |
| 4,900,672 A | 2/1990 | Yamada et al. | |
| 4,931,391 A | 6/1990 | Enomoto et al. | |
| 4,950,596 A | 8/1990 | Cheng et al. | |
| 4,950,956 A | 8/1990 | Asamaki et al. | |
| 6,251,646 B1 | 6/2001 | Dicosimo et al. | |
| 6,368,804 B1 | 4/2002 | Ben-Bassat et al. | |
| 6,649,382 B1 * | 11/2003 | Choi et al. | 435/158 |

FOREIGN PATENT DOCUMENTS

| | | |
|---|---|---|
| DE | 198 48 129 | 4/2000 |
| EP | 0 243 967 | 11/1987 |
| EP | 0 486 289 | 5/1992 |
| EP | 0 610 048 | 8/1994 |
| EP | 0 666 320 | 8/1995 |
| EP | 0 707 061 | 4/1996 |
| EP | 0 773 297 | 5/1997 |
| JP | 10194905 A * | 7/1998 |
| WO | WO-00/23577 | 4/2000 |

OTHER PUBLICATIONS

"Taber's Cyclopedic Medical Dictionary" Thomas, C. Editor. (1985)15th edition. (F.A. Davis Company: Philadelphia, PA) p. 1126.*
Sigma Catalog 1998 p. 536.*
Machine translation of JP 10194905 (1998) downloaded from the JPO Sep. 3, 2013.*
Bisignano et al. FEMS Microbiology Letters (2001) 198: 9-13.*
Morpeth et al. Biochemistry (1984) 23: 1332-1338.*
Suzuki et al. Biochem. Biophys. Res. Comm. (1981) 100(4): 1626-33.*
Kobayashi, M. et al., "Nitrilase of *Rhodococcus rhodochrous* J1, Purification and Characterization", Eur. J. Biochem. vol. 182 (1989), pp. 349-356.
Stevenson, D. E. et al., "Mechanistic and Structural Studies on *Rhodococcus* ATCC 39484 Nitrilase", Biotechnology and Applied Biochemistry, vol. 15 (1992), pp. 283-302.
Harper, D. B., "Purification and Properties of an Unusual Nitrilase from *Nocardia* N.C.I.B. 11216", Biochemical Society Transactions, vol. 4 (1976), pp. 502-504.
Harper, D. B., "Microbial Metabolism of Aromatic Nitriles: Enzymology of C-N Cleavage by *Nocardia* sp. (*Rhodochrous* Group) N.C.I.B. 11216", Hem. J., vol. 165 (1977), pp. 309-319.
Nagasawa, T. et al., "A Novel Nitrilase, Arylacetonitrilase, of *Alcaligenes faecalis* JM3, Purification and Characterization", Eur. J. Biochem. vol. 194 (1990), pp. 765-772.
Nagasawa, T. et al., "Nitrilase of *Rhodococcus rhodochrous* J1, Conversion into the Active Form by Subunit Association", Eur. J. Biochem, vol. 267 (2000), pp. 138-144.
Yamamoto, K. et al., "Purification and Characterization of the Nitrilase from *Alcaligenes faecalis* ATCC 8750 Responsible for Enantioselective Hydrolysis of Mandelonitrile", Journal of Fermentation and Bioengineering, vol. 73 (1992), pp. 425-430.
Willeman, W. F., et al., "Reaction Temperature Optimization Procedure for the Synthesis of (*R*)-mandelonitrile by *Prunus amygdalus* Hydroxynitrile Lyase Using a Process Model Approach", Enzyme and Microbial Technology, 2002, vol. 30, pp. 200-208.

* cited by examiner

*Primary Examiner* — Susan Hanley
(74) *Attorney, Agent, or Firm* — Drinker Biddle & Reath LLP

(57) ABSTRACT

The invention relates to a method for preserving and/or storing microorganisms which exhibit at least one nitrile hydratase or nitrilase enzyme activity, with the preservation and/or storage being effected in an aqueous medium which comprises at least one aldehyde, with the total aldehyde concentration being in a range from 0.1 to 100 mM/l.

20 Claims, 2 Drawing Sheets

METHODS FOR PRESERVING AND/OR STORING CELLS HAVING A NITRILASE OR NITRILE HYDRATASE ACTIVITY

RELATED APPLICATIONS

This application is a national stage application (under 35 U.S.C. 371) of PCT/EP2003/014880 filed Dec. 24, 2003 which claims benefit to German application 103 00 500.5 filed Jan. 8, 2003.

FIELD OF THE INVENTION

The invention relates to a method for preserving and/or storing microorganisms which exhibit at least one nitrile hydratase or nitrilase enzyme activity, with the preservation and/or storage being effected in an aqueous medium which comprises at least one aldehyde, with the total aldehyde concentration being in a range from 0.1 to 100 mM/l.

DESCRIPTION OF RELATED ART

Enzymes which are produced by microorganisms are being used increasingly as biocatalysts in chemical production processes. In particular, the enzymic hydrolysis of nitrites to give amides, carboxylic acids or α-hydroxycarboxylic acids is a process of great economic importance. Nitrile-hydrolyzing enzymes can be subdivided into the nitrile hydratase and nitrilase families. In their active centers, nitrile hydratases and nitrilases possess a cysteine molecule which is essential for the catalysis (Levy-Schil (1995) Gene 161:15-20). The nitrile hydratases catalyze the addition of one molar equivalent of water to give the corresponding amides. Nitrilases catalyze the addition of two molar equivalents of water to give the corresponding carboxylic acids. As a rule, the said enzymes bring about an optically selective hydration or hydrolysis, leading to optically active (chiral) products. Chiral carboxylic acids are sought-after compounds for synthetic organic chemistry. They are starting compounds for a large number of pharmaceutical active compounds or active compounds for plant protection. Chiral carboxylic acids can be used for the classical racemate resolution by way of diastereomeric salts. Thus, R-(−)- or S-(−)-mandelic acid is used, for example, for the racemate resolution of racemic amines. R-(−)-mandelic acid is also used as an intermediate in synthesis.

While purified or partially purified enzymes are usually employed for the enzymic reactions, it is also possible to use microorganisms which possess corresponding enzyme activities. The enzymes can be of natural or recombinant origin. As a rule, the enzymes are prepared (expressed) in a step which proceeds the reaction. In this connection, it is desirable to prepare relatively large quantities of enzyme and introduce these quantities into the catalytic process as needed. However, this makes it necessary to store the enzyme while retaining its activity. Cooling and/or freezing are standard methods in this connection. However, freezing usually requires complex freezing/thawing methods and is as a rule associated with a serious loss of enzyme activity. In general, cooling is associated with elaborate logistics and with energy costs.

EP-A1 0 666 320 describes a method for preparing α-hydroxyacids/amides from the corresponding nitrile, with the microorganisms employed being incubated in the presence of sodium sulfite (1 M) and phosphate buffer (50 mM) prior to the reaction. Furthermore, the enzyme activity can be further stabilized during the reaction by adding phosphite or hypophosphite, with said additions resulting in free, enzyme-inhibiting aldehyde being complexed. EP-A1 0 610 048 describes a microbial method for preparing α-hydroxyacids, with the enzyme activity being stabilized during the reaction by adding sodium sulfite, which likewise results in free, enzyme-inhibiting aldehyde being complexed. In said methods, the additives are without exception added during the conversion of the nitrile. Methods for stabilizing prior to use in the reaction have not been disclosed.

The typical method for preserving cysteine-dependent activities is that of adding dithiothreitol and/or mercaptoethanol and/or ethylenediaminetetraacetic acid (example: *Rhodococcus rhodochrous* J1 nitrilase; Kobayashi M (1989) Eur J Biochem 182: 349-356).

The stabilization of *Rhodococcus* sp. ATCC 39484 nitrilase was achieved by adding substrate (benzonitrile) (Stevenson D E (1992) Biotechnol Appl Biochem 15:283-302). In the case of *Rhodococcus rhodochrous* NCIB 11216 nitrilase, a basic pH, the temperature and the enzyme concentration are responsible, in addition to the substrate concentration, for the speed of the stabilization (Harper B H (1976) Biochem Soc Trans 4:502-504; Harper B H (1977) Biochem J 165:309-319). A disadvantage in these cases is that the stabilizer is transformed by the enzyme and consequently loses its effect over time.

The addition of inorganic salts (including up to 20% $(NH_4)_2SO_4$) and alcohols (up to 50% glycerol, 10% ethanol) for the purpose of stabilizing enzyme activity has been described in the case of *Rhodococcus rhodochrous* J1 nitrilase (Nagasawa T (2000) Eur J Biochem 267:138-144).

The addition of 60% ammonium sulfate, 2M NaCl or 30% propanediol for the purpose of stabilizing enzyme activity has been described in the case of Alcaligenes faecalis JM3 nitrilase (Nagasawa T (1990) Eur J Biochem 194:765-772).

EP-A1 0 707 061 describes methods for stabilizing nitrilase-comprising cells by adding inorganic salts (phosphates, borates, sulfates, sulfites and hydrochlorides), at concentrations of at least 100 mM up to the saturation limit, to the storage buffer.

U.S. Pat. No. 4,931,391, EP-A1 0 243 967 and U.S. Pat. No. 4,900,672 describe the stabilization of a nitrile hydratase activity by adding amides or carboxylic acids (or a combination of substances) to the cell suspension.

U.S. Pat. No. 4,343,900 describes a method for producing acrylamide from acrylonitrile, with alkali metal carbonates being added to the reaction mixture for the purpose of avoiding the loss of activity in connection with the swelling of the fixed cells which are used.

U.S. Pat. Nos. 6,251,646 and 6,368,804 describe methods for stabilizing nitrilase activity-harboring microorganisms by adding ammonium, sodium or potassium (hydrogen) carbonates at concentrations of from at least 0.1 M up to the saturation concentration.

Because of the reactive aldehyde group, aldehydes are classified as being enzyme-inhibiting substances. Their inhibitory effect on nitrilases during the production process is emphasized in a large number of publications (EP-B1 0 773 297 B1, p. 4 paragraphs [0013] and [0025]; EP-B1 0 707 061 B1, p. 2 paragraph [0005]; EP-B1 0 666 320, p. 2 paragraph [0004] and the literature references which are cited at that point; EP-A2 0 486 289 p. 2 line 30, and the literature references which are cited at that point; Yamamoto (1992) J Ferm Technol 73:425-430, in particular p. 429 last paragraph).

The inactivation of the nitrilase/nitrile hydratase activity during storage is an important cost factor in connection with using said enzymes industrially. For example, at 4° C. and pH 6.0, the activity decreases by 36% over a period of 6.6 days, denoting an activity loss of 5.5% per day (cf. FIG. 1; comparison experiments in Example 3). Loss of activity in the case of nitrilases can be due, for example, to the enzyme multimer decomposing into its monomers, which do not possess any nitrilase activity (Nagasawa T (1990) Eur J Biochem 194:765-772). The described methods are only to a very limited extent able to solve this problem. Furthermore, said methods use high concentrations of additives for stabilizing the biocatalysts, which additives have furthermore to be separated off, and disposed of, in an elaborate manner after the biocatalyst has been used.

The object underlying the present invention was consequently that of providing a method which enables a nitrilase/nitrile hydratase activity to be stabilized for as long as possible without the reaction mixture being contaminated with unwanted attendant substances.

DETAILED DESCRIPTION OF THE INVENTION

Figure 1:
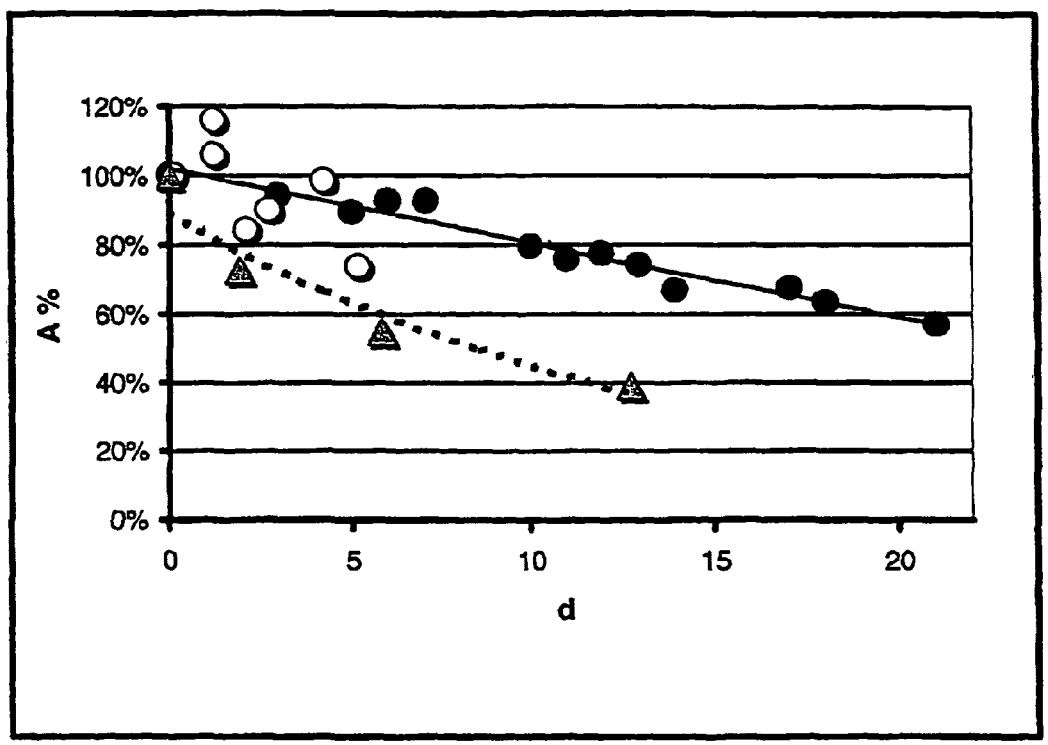
FIG. 1: Storage stability of a nitrilase for producing (R)-mandelic acid. The figure depicts, by way of example, the decrease in the activity (A; in % of the initial activity) of three independent preparations of an $E.$ $coli$-expressed nitrilase without added aldehyde (comparison experiments) over a period of up to 20 days (d).

The method according to the invention achieves this object.

A first step in the invention relates to a method for preserving and/or storing microorganisms which possess at least one nitrile hydratase or nitrilase enzyme activity, with the preservation and/or storage being effected in an aqueous medium which comprises at least one aldehyde, with the total aldehyde concentration being in a range from 0.1 to 100 mM/l.

Said preservation step is preferably carried out before the cells are treated with a reactant whose reaction is to be catalyzed by the cells. In a preferred embodiment, the aqueous medium comprises a total concentration of cyanide compounds, which are selected from the group consisting of nitrites, hydrocyanic acid and cyanide salts, which is at most 10 mol % of the total aldehyde concentration. In a particularly preferred embodiment, the aqueous medium which is suitable for the preservation and/or storage does not comprise any additions of said cyanide compounds.

The term "aldehyde" is to be understood broadly and encompasses both aliphatic and aromatic aldehydes. In a preferred embodiment, aldehyde means compounds of the formula III:

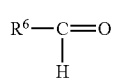

(III)

where $R^6$ can be substituted or unsubstituted, branched or unbranched, C1-C10-alkyl-, C2-C10-alkenyl-, or substituted or unsubstituted aryl- or hetaryl-. Particular preference is given to aromatic aldehydes, with very particular preference being given to unsubstituted benzaldehyde and substituted benzaldehydes, such as o-chlorobenzaldehyde, m-chlorobenzaldehyde, p-chlorobenzaldehyde, o-bromobenzaldehyde, m-bromobenzaldehyde, p-bromobenzaldehyde, o-methylbenzaldehyde, m-methylbenzaldehyde and p-methylbenzaldehyde.

The preserved/stored microorganisms can be used, for example, for converting racemic nitriles of the formula (II) into chiral carboxylic acids of the formula (Ia) or chiral amides of the formula (Ib):

(Ia)

(Ib)

(II)

* an optically active center $R^1$, $R^2$ and $R^3$ are, independently of each other, hydrogen, substituted or unsubstituted, branched or unbranched, C1-C10-alkyl-, C2-C10-alkenyl-, substituted or unsubstituted aryl-, hetaryl-, $OR^4$ or $NR^4R^5$, and where the radicals $R^1$, $R^2$ and $R^3$ are always different, $R^4$ is hydrogen, substituted or unsubstituted, branched or unbranched, C1-C10-alkyl-, C2-C10-alkenyl-, C1-C10-alkylcarbonyl-, C2-C10-alkenylcarbonyl-, aryl-, arylcarbonyl-, hetaryl- or hetarylcarbonyl-, $R^5$ is hydrogen, substituted or unsubstituted, branched or unbranched, C1-C10-alkyl-, C2-C10-alkenyl-, aryl- or hetaryl-.

Nitriles which are most preferred are mandelonitrile, o-chloromandelonitrile, p-chloromandelonitrile, m-chloromandelonitrile, o-bromomandelonitrile, p-bromomandelonitrile, m-bromomandelonitrile, o-methylmandelonitrile, p-methylmandelonitrile or m-methylmandelonitrile. The most preferred chiral carboxylic acids are R-mandelic acid, S-mandelic acid, R-p-chloromandelic acid, S-p-chloromandelic acid, R-m-chloromandelic acid, S-m-chloromandelic acid, R-o-chloromandelic acid, S-o-chloromandelic acid, S-o-bromomandelic acid, S-p-bromomandelic acid, S-m-bromomandelic acid, S-o-methylmandelic acid, S-p-methylmandelic acid, S-m-methylmandelic acid, R-o-bromomandelic acid, R-p-bromomandelic acid, R-m-bromomandelic acid, R-o-methylmandelic acid, R-p-methylmandelic acid and R-m-methylmandelic acid.

If α-hydroxy nitriles of the formula (IV)

(IV)

(where the same definition as in formula (III) applies in the case of $R^6$) are used as starting compounds for the sought-after nitrilase/nitrile hydratase-catalyzed reaction, the aldehyde employed for the preservation/storage is then preferably the same aldehyde which yields said α-hydroxynitrile by reaction with hydrocyanic acid or cyanide, i.e. the radical $R^6$ is preferably chosen identically in the formulae III and IV.

The total concentration of aldehydes in the aqueous medium which is suitable for the preservation and/or storage is from 0.1 to 100 mM/l, preferably from 0.2 to 50 mM/l, particularly preferably from 0.5 to 10 mM/l, very particularly preferably from 0.3 to 5 mM/l, most preferably from 0.4 to 2 mM/l.

The aqueous medium can have a neutral, weakly basic or weakly acidic pH. Accordingly, the pH is in a range from pH 6 to 8, preferably pH 6.5 to 7.5. The preservation temperature is preferably in a range from 0 to 40° C., particularly preferably from 1 to 10° C., very particularly preferably from 2 to 5° C.

The method according to the invention has proved, both under laboratory conditions and under production conditions, to be extremely suitable for ensuring long-lasting enzyme activity. The biocatalyst does not exhibit any inactivation within the observed period of 37 days.

Within the context of this invention, "microorganism" means Gram-positive or Gram-negative bacteria.

Preference is given to all genera and species of the Enterobacteriaceae, or families, and of the order Actinomycetales, with very particular preference being given to the Enterobacteriaceae species *Escherichia, Serratia, Proteus, Enterobacter, Klebsiella, Salmonella, Shigella, Edwardsielle, Citrobacter, Morganella, Providencia* and *Yersinia*.

Preference is furthermore given to the species *Pseudomonas, Burkholderia, Nocardia, Acetobacter, Gluconobacter, Corynebacterium, Brevibacterium, Bacillus, Clostridium, Cyanobacter, Staphylococcus, Aerobacter, Alcaligenes, Rhodococcus* and *Penicillium*.

Most preference is given to *Escherichia* species, in particular *Escherichia coli*.

During the method according to the invention, the microorganism can be present in a growing, resting, immobilized or disrupted state. "Disrupted cells" are to be understood, for example, as being cells which have been made permeable by a treatment with solvents, for example, or cells which have been broken open by means of an enzyme treatment, by means of mechanical treatment (e.g. French press or ultrasonication) or by means of another method. The crude extracts which are obtained in this way are advantageously suitable for the method according to the invention. Partially or completely purified enzyme preparations can also be used for the method. Immobilized microorganisms or enzymes, which can advantageously be used in reaction, are likewise suitable. The immobilization can be effected, for example, by adding one or more acrylic monomers (for example acrylamide, acrylic acid, methacrylamide, methacrylic acid, N,N-dimethylacrylamide, N,N-diethylacrylamide, dimethylaminopropyl acrylate, dimethylaminopropyl methacrylate, dimethylaminopropylacrylamide, dimethylaminopropylmethacrylamide, diethylaminopropylacrylamide or diethylaminopropylmethacrylamide) and also, where appropriate, one or more crosslinking agents (e.g. methylenebisacrylamide, methylenebismethacrylamide, 1,2-dihydroxyethylenebisacrylamide or bisacrylamidoacetic acid) to the cell or enzyme preparation and then carrying out free-radical polymerization (initiated by, for example, ammonium persulfate).

In order to prevent contamination with foreign bacteria or fungi, suitable active compounds having an antibacterial or fungicidal effect, or other salts, such as ethylenediaminetetraacetic acid, can be added, where appropriate, to the preservation/storage solution.

The microorganisms which are used in methods according to the invention can, prior to preservation/storage, be cultured in a medium which enables these organisms to grow. This medium can be a synthetic medium or a natural medium. Media known to the skilled person are used depending on the organism. To enable the microorganisms to grow, the media employed comprise a carbon source, a nitrogen source, inorganic salts and, where appropriate, small quantities of vitamins and trace elements.

Examples of advantageous carbon sources are polyols, such as glycerol, sugars, such as mono-, di- or polysaccharides, such as glucose, fructose, mannose, xylose, galactose, ribose, sorbose, ribulose, lactose, maltose, sucrose, raffinose, starch or cellulose, complex sugar sources, such as melasse, sugar phosphates, such as fructose-1,6-diphosphate, sugar alcohols, such as mannitol, alcohols, such as methanol or ethanol, carboxylic acids, such as citric acid, lactic acid or acetic acid, fats, such as soybean oil or rapeseed oil, amino acids, such as an amino acid mixture, for example Casamino acids (Difco) or individual amino acids, such as glycine or aspartic acid, or amino sugars; the latter can also be used simultaneously as the nitrogen source. Particular preference is given to polyols, in particular glycerol.

Advantageous nitrogen sources are organic or inorganic nitrogen compounds or materials which comprise these compounds. Examples are ammonium salts, such as $NH_4Cl$ or $(NH_4)_2SO_4$, nitrates, urea, or complex nitrogen sources such as corn steep liquor, beer yeast autolysate, soyabean meal, wheat gluten, yeast extract, peptone, meat extract, caseine hydrolysate, yeast or potato protein, which can frequently also simultaneously be used as the nitrogen source.

Examples of inorganic salts are the salts of calcium, magnesium, sodium, cobalt, molybdenum, manganese, potassium, zinc, copper and iron. Anions of these salts which may in particular be mentioned are the chlorine, sulfate and phosphate ions. An important factor for increasing productivity in the method according to the invention is the control of the $Fe^{2+}$ or $Fe^{3+}$-ion concentration in the production medium.

Where appropriate, other growth factors, such as vitamins or growth promoters, such as biotin, 2-KLG, thiamine, folic acid, nicotic acid, pantothenate or pyridoxine, amino acids, such as alanine, cysteine, proline, aspartic acid, glutamine, serine, phenylalanine, ornithine or valine, carboxylic acids, such as citric acid, formic acid, pimelic acid or lactic acid, or substances such as dithiothreitol, are added to the nutrient medium.

The ratio in which said nutrients are mixed depends on the nature of the fermentation and is specified in each individual case. The medium components can all be introduced at the beginning of the fermentation, after they have, if necessary, been sterilized separately or sterilized jointly, or else be subsequently added during fermentation, continuously or discontinuously, as required.

The culture conditions are specified such that the organisms grow so as to achieve the best possible yield (to be determined, for example, by the total activity of the recombinant protein which is expressed). Preferred culture temperatures are from 15° C. to 40° C. Temperatures of between 25° C. and 37° C. are particularly advantageous. The pH is preferably maintained in a range from 3 to 9. pH values of between 5 and 8 are particularly advantageous. In general, an incubation period of from a few hours to a few days, preferably of from 8 hours to 21 days, particularly preferably of from 4 hours to 14 days, is sufficient.

The skilled person can, for example, obtain information with regard to advantageously optimizing media from the textbook Applied Microbiol Physiology, "A Practical Approach (Eds. P M Rhodes, P F Stanbury, IRL-Press, 1997, pp. 53-73, ISBN 0 19 963577 3).

The aldehyde can be added, for the purpose of preservation/storage, prior to, during or after the culture of the microorganisms. Thus, it is possible, for example, to achieve maximum preservation of the activity by adding the aldehyde to the fermentation mixture without any further separation of the microorganisms.

However, it is likewise possible to separate the microbial cells or microorganisms, which have been cultured in this way, by, for example, centrifuging them from the culture medium, optionally washing them once, or several times, with a suitable buffer (such as a borate buffer or phosphate buffer) and then, for the purpose of storage/preservation, taking them up, or resuspending them, in the aqueous solution, which comprises at least one aldehyde. The concentration of the microorganisms in said aqueous solution comprising at least one aldehyde can be selected at will.

The microorganisms which are used within the context of the invention exhibit at least one nitrile hydratase and/or nitrilase activity.

In a general manner, "nitrile hydratase" activity means the property of catalyzing the addition of one molar equivalent of water to a nitrile, thereby forming the corresponding amide:

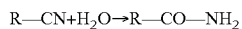

R—CN+H$_2$O→R—CO—NH$_2$ nitrile hydratases preferably comprise enzymes of the EC class 4.2.1.84 (nitrile hydratases).

In a general manner, "nitrilase" activity means the property of catalyzing the addition of two molar equivalents of water to a nitrile, thereby forming the corresponding carboxylic acid:

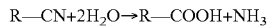

R—CN+2H$_2$O→R—COOH+NH$_3$

Nitrilases preferably comprise enzymes of the EC classes 3.5.5.1 (nitrilases), 3.5.5.2 (ricinin nitrilase), 3.5.5.4 (cyanoalanine nitrilases), 3.5.5.5 (arylacetonitrilases), 3.5.5.6 (bromoxynil nitrilases) and 3.5.5.7 (aliphatic nitrilases).

The nitrilase and/or nitrile hydratase activity of said microorganism cells can be of natural or recombinant origin.

In this connection, "of natural origin" means that the microorganism as such, without any genetic change brought about by human action, exhibits a corresponding nitrilase and/or nitrile hydratase activity. A large number of such microorganisms are known to the skilled person. Preference is given, in particular, to microorganisms of the genera *Rhodococcus* and Gordona, such as *Rhodococcus* sp. HT40-6 (FERM BP-5231), *Rhodococcus rhodochrous* ATCC 33278, *Rhodococcus rhodochrous* J-1 (FERM BP-1478) and Gordona terrae MA-1 (FERM BP-4535) (JP-A-4-222591, JP-B-6-55148, EP-A1 0 707 061).

In this connection, "of recombinant origin" means that the DNA sequence encoding an enzyme possessing nitrilase and/or nitrile hydratase activity is isolated from a microorganism and expressed in a microorganism of another species. Numerous sequences encoding enzymes possessing nitrilase and/or nitrile hydratase activity are known to the skilled person. The following may be mentioned by way of example but not in a limiting manner:

1. *Acidovorax facilis* nitrilase 72W (Gavagan J E et al. (1999) Appl Microbiol Biotechnol 52:654-659)
2. *Acinetobacter* sp. AK 226 nitrilase (Yamamoto K and Komatsu K (1991) Agric Biol Chem 55(6):1459-1466)
3. *Acinetobacter* sp. RFB1 nitrilase (Finnegan I et al. (1991) Appl Microbiol Biotechnol 36:142-144)
4. *Alcaligenes faecalis* ATCC 8750 nitrilase (Yamamoto K et al. (1991) Appl Environ Microbiol 57(10):3028-3032)
5. *Alcaligenes faecalis* JM3 nitrilase (Nagasawa T et al. (1990) Eur J Biochem 194:765-772)
6. *Arabidopsis thaliana* nitrilases (NIT1/NIT2/NIT3) (Vorwerk S et al. (2001) Planta 212:508-516
7. *Arthrobacter* sp. J-1 nitrilase (Bandyopadhyay A K et al. (1986) Appl Environ Microbiol 51(2):302-306)
8. *Bacillus pallidus* Dac521 nitrilase (Cramp R et al. (1997) Microbiology 143:2313-2320)
9. *Comamonas* sp. NI1 nitrilase (Cerbelaud E et al. (1996) Ind Chem Libr 8:189-200)
10. *Comamonas testosteroni* sp. nitrilase (Levy-Schil S et al. (1995) Gene 161:15-20)
11. *Fusarium oxysporum* f. sp. melonis nitrilase (Goldlust A and Bohak Z (1989) Biotechnol Appl Biochem 11:581-601)
12. *Fusarium solani* nitrilase (Harper B H (1977) Biochem J 167:685-692)
13. *Klebsiella ozaenae* nitrilase (McBride K E et al. (1986) Appl Environ Microbiol 52(2):325-330)
14. *Pseudomonas fluoreszenz* DSM 7155 nitrilase (Layh N et al. (1998) J Mol Catal B: Enzym 5:467-474)
15. *Pseudomonas* sp. nitrilase (Layh N et al. (1992) Arch Microbiol 158:405-411)
16. *Pseudomonas* sp. (S1) nitrilase (Dhillon J et al. (1999) Can J Microbiol 45: 811-815)
17. *Pseudomonas* sp. 13 nitrilase (Yanase H et al. (1982) Agric Biol Chem 46:2925)
18. *Rhodococcus rhodochrous* J1 nitrilase (Kobayashi M et al. (1989) Eur J Biochem 182:349-356)
19. *Rhodococcus rhodochrous* K22 nitrilase (Kobayashi M et al. (1990) J Bacteriol 172(9):4807-4815)
20. *Rhodococcus rhodochrous* NCIB 11215 nitrilase (Harper B H (1985) Int J Biochem 17(6):677-683)
21. *Rhodococcus rhodochrous* NCIB 11216 nitrilase (Harper B H (1977) Biochem J 165:309-319)
22. *Rhodococcus rhodochrous* PA34 nitrilase (Bhalla T C et al. (1992) Appl Microbiol Biotechnol 37:184-190)
23. *Rhodococcus* sp. ATCC 39484 nitrilase (Stevenson D E et al. (1992) Biotechnol Appl Biochem 15:283-302)

In a preferred embodiment, the nitrilase is described by an amino acid sequence which is encoded by a nucleic acid sequence which is selected from the group
a) a nucleic acid sequence having the sequence depicted in SEQ ID NO: 1,
b) nucleic acid sequences which are derived from the nucleic acid sequence depicted in SEQ ID NO: 1 as a result of the degeneracy of the genetic code,
c) derivatives of the nucleic acid sequence depicted in SEQ ID NO: 1 which encode polypeptides having the amino acid sequences depicted in SEQ ID NO: 2 and exhibit at least 35% homology at the amino acid level and are able to convert at least one nitrile into the corresponding carboxylic acid.

The expression of recombinant nitrilases/nitrile hydratases can be effected, for example, using a suitable DNA construct which has been introduced into the microorganism. The DNA construct is preferably a vector. Vectors can, by way of example, be plasmids, cosmids or phages. Preference is given to the vector being a circular plasmid which comprises the nucleic acid sequence being expressed in recombinant form and which is capable of autonomous replication in the prokaryotic host cell. Vectors which may be mentioned by way of example are:
a) preferably pQE70, pQE60 and pQE-9 (QIAGEN, Inc.); pBluescript vectors, Phagescript vectors, pNH8A, pNH16a, pNH18A, pNH46A (Stratagene Cloning Systems, Inc.); ptrc99a, pKK223-3, pKK233-3, pDR540, pRIT5 (Pharmacia Biotech, Inc.); pLG338, pACYC184, pBR322, pUC18, pUC19, pKC30, pRep4, pHS1, pHS2, pPLc236, pMBL24, pLG200, pUR290, pIN-III[113]-B1, λgt11 or pBdCI in *E. coli*, b) preferably pIJ101, pIJ364, pIJ702 or pIJ361 in *Streptomyces*, c) preferably pUB110, pC194 or pBD214 in *Bacillus*, d) pSA77 or pAJ667 in *Corynebacterium*, or derivatives of the abovementioned plasmids. Said plasmids constitute a small selection of the possible plasmids. Other plasmids are well known to the skilled person and are listed, for example, in the book Cloning Vectors (Eds. Pouwels P. H. et al. Elsevier, Amsterdam-New York-Oxford, 1985, ISBN 0 444 904018).

The DNA construct comprises at least one nucleic acid sequence which is to be expressed, which encodes an enzyme having nitrilase and/or nitrile hydratase activity and which is functionally linked to a promoter which functions in the particular microorganism which is being used.

A large number of promoters which function in microorganisms are known to the skilled person: promoters such as the cos, tac, trp, tet, lpp, lac, lacIq, T7, T5, T3, gal, trc, ara, rha, SP6, λ-PR or λ-PL promoters may be mentioned by way of example. Particular preference is given to the *E. coli* rhamnose operon promoter (rha promoter), which can be induced by adding rhamnose.

In a general manner, a functional linkage is understood as being an arrangement in which a genetic control sequence (e.g. a promoter) is able to exert its function in relation to the nucleic acid sequence which is to be expressed. In this connection, function can, for example, denote control of the expression, i.e. transcription and/or translation, of the nucleic acid sequence. In this connection, control comprises, for example, the initiation, increase, regulation or suppression of the expression, i.e. transcription and, where appropriate, translation. A functional linkage is understood, for example, as being the sequential arrangement of a promoter, of the nucleic acid sequence to be expressed and, where appropriate, of other regulatory elements, such as a terminator, such that each of the regulatory elements is able to fulfill its function in connection with the expression of the nucleic acid sequence. The skilled person is familiar with a variety of ways for obtaining one of the DNA constructs according to the invention. The DNA construct can be prepared using customary recombination and cloning techniques, as are described, for example, in T Maniatis, E F Fritsch and J Sambrook, Molecular Cloning: A Laboratory Manual, Cold Spring Harbor Laboratory, Cold Spring Harbor, N.Y. (1989) and in T J Silhavy, M L Berman and L W Enquist, Experiments with Gene Fusions, Cold Spring Harbor Laboratory, Cold Spring Harbor, N.Y. (1984) and in Ausubel, F M et al., Current Protocols in Molecular Biology, Greene Publishing Assoc. and Wiley Interscience (1987).

Said DNA construct can comprise additional functional elements. The term functional elements is to be understood broadly and means all those sequences which exert an effect on the genesis, the replication or the function of the DNA constructs or organisms according to the invention. For example, functional elements ensure, augment, regulate or modify transcription and, where appropriate, translation in corresponding host organisms.

Functional elements are described, for example, in "Goeddel; Gene Expression Technology: Methods in Enzymology 185, Academic Press, San Diego, Calif. (1990)" or "Gruber and Crosby, in: Methods in Plant Molecular Biology and Biotechnology, CRC Press, Boca Raton, Fla., eds.: Glick and Thompson, Chapter 7, 89-108", as well as in the citations which are contained in these publications. Different control sequences are suitable depending on the host organism or starting organism which is described in more detail below and which is converted into a genetically altered or transgenic organism as a result of introducing the expression cassettes or vectors.

"Genetic control sequences" comprise, for example, the 5'-untranslated region or the noncoding 3' region of genes. In addition, the term "genetic control sequences" means sequences which encode fusion proteins which consist of a signal peptide sequence. The following may be mentioned by way of example but in a nonlimiting manner:

a) Selection Markers

Selection markers are as a rule required for successfully selecting transformed cells and for preventing the loss of the DNA construct from the host cell over time and during cell divisions. Such a loss can, in particular, occur if the recombinant protein which is encoded by the nucleic acid sequence to be expressed has a toxic effect on the prokaryotic organism. The selectable marker which is introduced together with the expression construct confers resistance to a biocide (for example an antibiotic such as ampicillin, kanamycin or hygromycin) on the cells which have been successfully transformed. Selection markers which may be mentioned by way of example are:

Amp (ampicillin resistance; b-lactamase)
Cab (carbenicillin resistance)
Cam (chloramphenicol resistance)
Kan (kanamycin resistance)
Rif (rifampicin resistance)
Tet (tetracycline resistance)
Zeo (zeocin resistance)
Spec (spectinomycin)

The selection pressure is maintained by using appropriate quantities of the antibiotic. The following may be mentioned by way of example: ampicillin, 100 mg/l, carbenicillin, 100 mg/l, chloramphenicol, 35 mg/l, kanamycin, 30 mg/l, rifampicin, 200 mg/l, tetracycline, 12.5 mg/l and spectinomycin, 50 mg/l.

Selection markers furthermore comprise genes and gene products which, by, for example, complementing a genetic deficiency in the amino acid or nucleotide synthesis, enable a correspondingly transformed host cell to be selected. Media which do not comprise said amino acid or said nucleotide building block are used, inter alia, for this purpose. The skilled person is familiar with a variety of such systems. The deficiencies in tryptophan (e.g. trpC), leucine (e.g. leuB) and histidine (e.g. hisB) biosynthesis, as are present, for example, in the *E. coli* strain KC8 (Clontech), may be mentioned by way of example. These deficiencies can be complemented, inter alia, by the selectable markers TRP1, Leu2 and HIS3.

b) Transcription Terminators

The transcription terminator reduces an unwanted transcription and increases plasmid and mRNA stability.

c) Shine-Dalgarno Sequences

A Shine-Dalgarno (SD) sequence is required for initiating translation and is complementary to the 3' end of 16S ribosomal RNA. The efficiency of the initiation of translation at the start codon depends on the actual sequence. An example of a consensus sequence suitable for *E. coli* is: 5'-TAAGGAGG-3'. It is located approx. 4 to 14 nucleotides upstream of the start codon, with the optimum being 8 nucleotides. In order to avoid the formation of secondary structures (which can reduce expression), this region should preferably be rich in A/T nucleotides.

d) Start Codon

The start codon is the point at which translation is initiated. ATG is the start codon which is used the most in *E. coli*; GTG can also be used as an alternative.

e) Tags and Fusion Proteins

N-or C-terminal fusions of the recombinant proteins to be expressed with relatively short peptides (tags) or other proteins (fusion partners) may be advantageous. They can, for example, make it possible to achieve improvements in expression, solubility, detectability and purification. Preference is given to combining such fusions with protease cleavage sequences (e.g. for thrombin or factor X) which make it possible to remove the tags or the fusion partner following expression and purification.

f) Multiple Cloning Regions (Multiple Cloning Site; MCS) Permit and Facilitate the Insertion of One or More Nucleic Acid Sequences.

g) Stop Codon/Translation Terminators

Of the three possible stop codons, preference is given to TAA since read-through, without any termination of the translation, may possibly occur when TAG and TGA are used. A sequence of several stop codons may also be used in order to ensure reliable termination.

h) Reporter Genes

Reporter genes encode readily quantifiable proteins which, by way of intrinsic color or enzyme activity, make it possible to assess the efficiency of transformation, the level of expression and the site or time of expression. Reporter genes can, for example, encode the following proteins: hydrolases, fluorescent proteins, bioluminescent proteins, glucosidases or peroxidases. Preference is given to luciferases, β-galactosidases, β-glucuronidase, green fluorescence protein, acetyl transferases, phosphotransferases and adenyltransferases (see also Schenborn E, Groskreutz D (1999) Mol Biotechnol 13(1):29-44).

The preparation of a transformed microorganisms requires the corresponding DNA (for example one of the expression cassettes or vectors according to the invention) to be introduced into the corresponding host cell. A large number of methods are available for this procedure, which is termed transformation (see also Keown et al. (1990) Methods in Enzymology 185:527-537). Thus, the DNA can, by way of example, be introduced directly by means of microinjection or electroporation or by means of bombarding with DNA-coded microparticles (biolistic method using a particle-bombardment gene cannon). It is also possible to permeabilize the cell chemically, for example using polyethylene glycol, such that the DNA is able to gain entry into the cell by means of diffusion. The DNA [lacuna] can also be effected by means of fusion with other DNA-containing units such as minicells, cells, lysosomes or liposomes. Electroporation, in which the cells are permeabilized reversibly by means of an electric impulse, is another suitable method for inserting DNA. Preferred general methods which may be mentioned are calcium phosphate-mediated transformation, DEAE dextran-mediated transformation, cationic lipid-mediated transformation, electroporation, transduction and infection. These methods are familiar to the skilled person and are, for example, described (Davis et al. (1986) Basic Methods In Molecular Biology; Sambrook J et al. (1989) Molecular cloning: A laboratory manual, Cold Spring Harbor Laboratory Press; Ausubel F M et al. (1994) Current protocols in molecular biology, John Wiley and Sons; Glover D M et al. (1995) DNA Cloning Vol. 1, IRL Press ISBN 019-963476-9).

Transformed cells, that is those which comprise the inserted DNA, can be selected from untransformed cells if a selectable marker forms part of the inserted DNA. A variety of selection markers are described above.

The invention furthermore relates to a preparation of microorganisms which contain at least one nitrile hydratase or a nitrilase enzyme activity, with the preparation comprising a) at least one aldehyde giving a total aldehyde concentration in a range from 0.1 to 100 mM/l, and b) cyanide compounds, selected in the group consisting of nitrites, hydrocyanic acid and cyanide salts, at a total concentration which it at most 10 mol % of the total aldehyde concentration.

In a particularly preferred embodiment, the preparation according to the invention does not contain any additions of said cyanide compounds.

The invention furthermore relates to the use of the preparation of microorganisms according to the invention for producing foodstuffs, feedstuffs, pharmaceuticals or fine chemicals. "Fine chemicals" preferably means proteins, enzymes, vitamins, amino acids, sugars, fatty acids and natural and synthetic flavoring agents, aromatizing agents and dyes.

The invention furthermore relates to methods for preparing recombinant proteins, enzymes (preferably enzymes possessing nitrilase and/or nitrile hydratase activity) or other fine chemicals such as amides or carboxylic acids (preferably chiral carboxylic acids and amides) using one of the preparation of microorganisms according to the invention or a preparation thereof.

A preferred part of the subject-matter of the invention relates to a method for preparing carboxylic acids and/or amides (preferably chiral carboxylic acids/amides), comprising the following steps:

a) culturing a microorganism which possesses at least one nitrile hydratase or nitrilase enzyme activity, b) adding at least one aldehyde, with the total aldehyde concentration being in the range from 0.1 to 100 mM/l, c) bringing the aldehyde-treated preparation of said microorganisms into contact with at least one nitrile and converting said nitrile into a carboxylic acid and/or an amide.

In a preferred embodiment, the preparation of the microorganism comprises, in connection with the addition of the aldehyde, cyanide compounds, selected from the group consisting of nitrites, hydrocyanic acid and cyanide salts, at a concentration which is at most 10 mol % of the total aldehyde concentration. In a particularly preferred embodiment, said preparation does not contain any additions of said cyanide compounds. In an embodiment which is furthermore preferred, the preparation can, after the addition of the aldehyde (step b), be stored until being used in reaction step c). The method according to the invention can be carried out continuously or discontinuously in batch mode or fed-batch mode. In this connection, both the preparation of the microorganisms and the racemic nitrile, as substrate, can be added subsequently.

Details with regard to carrying out the reactions and/or with regard to purifying the products, etc., are described in detail, for example, in WO 00/23577. The starting compounds, products and methological parameters described in that publication are hereby expressly incorporated by reference.

In another preferred embodiment, the method can be combined with other methods for stabilizing, preserving and/or storing enzymes, in particular nitrilases and/or nitrile hydratases. These methods can, by way of example but not in a limiting manner, comprise:

a) Adding at least one inorganic salt (preferably selected from the group consisting of phosphates, borates, sulfates, sulfites and hydrochlorides) at a concentration of at least 100 mM, preferably from 300 to 700 mM.

b) Adding metal salts whose metal cation functions as a nitrilase and/or nitrile hydratase prosthetic group (e.g. cobalt chloride or iron sulfate).

c) Adding nitrites (e.g. benzonitrile, isobutyronitrile or succinonitrile) and/or amides (s-caprolactam, isobutylamide or propionamide).

EXAMPLES

Unless otherwise described, general nucleic acid methods, such as cloning, restriction cleavages, agarose gel electrophoreses, linking of DNA fragments, transformation of microorganisms, growth of bacteria and analysis of recombinant DNA sequences, were carried out as described in Sambrook et al. (1989) (Cold Spring Harbor Laboratory Press: ISBN 0-87969-309-6). Recombinant DNA molecules were sequenced by the Sanger method (Sanger et al. (1977) Proc. Natl. Acad. Sci. USA 74:5463-5467) using an ABI laser-fluorescence DNA sequencer. In order to avoid polymerase errors in constructs to be expressed, fragments resulting from a polymerase chain reaction were sequenced and checked.

Example 1

Preparing Cells Possessing Nitrilase Activity

The *Escherichia coli* strain (TG10 pDHE1650 pAgro4 pHSG575) was fermented in a 20 l bioreactor. The reactor, containing a 10 l working volume, was inoculated with 200 ml of preliminary culture from shaker flasks. The preliminary culture medium corresponds to the main culture medium.
Medium:

| | |
|---|---|
| 40 g | of 99.5% glycerol |
| 15 g | of tryptone |
| 13.3 g | of potassium dihydrogen phosphate |
| 5 g | of yeast extract |
| 4 g | of diammonium hydrogen phosphate |
| 1.7 g | of citric acid |
| 1.1 g | of magnesium sulfate heptahydrate |
| 1 ml | of SL Korz 1000 C trace element solution |
| 0.1 ml | of Tego KS 911 antifoaming agent |
| 0.062 g | of iron(II) sulfate heptahydrate |
| 10 mg | of thiamine hydrochloride |
| to 1 l | deionized water |

The medium is sterilized at 121° C. for 30 min. 0.1 g of ampicilin is then added under sterile conditions.

Trace Element Solution

| | | |
|---|---|---|
| Citric acid*H2O | | 20 g |
| Cobalt(II) chloride hexachloride | CoCl$_2$ * 6H$_2$O | 2.5 g |
| Manganese(II) chloride tetrachloride | MnCl$_2$ * 4H$_2$O | 3.0 g |
| Copper(II) chloride dihydrate | CuCl$_2$ * 2H$_2$O | 0.3 g |
| Boric acid | H$_3$BO$_3$ | 0.6 g |
| Sodium molybdate dihydrate | Na$_2$MoO4 * 2H$_2$O | 0.5 g |
| Zinc acetate dehydrate | Zn(CH$_3$COO)$_2$ * 2H$_2$O | 2.6 g |
| to 1 l deionized H2O | | |

Glycerol Feed Solution

| | |
|---|---|
| 2 l | of deionized water |
| 211 g | of sodium sulfate |
| 13.6 g | of iron(II) sulfate heptahydrate |
| 8.8 kg | of 99.5% glycerol |
| 220 ml | of trace element solution |

Rhamnose Feed Solution

| | |
|---|---|
| 703 g | of deionized water |
| 297 g | of rhamnose monohydrate |

The fermentation is carried out at a temperature of 37° C. The gassing is regulated between 8-30 l/min, while the rotation speed of the stirrer is regulated at 400-1500 l/min, in order to maintain a pO$_2$ of not less than 20%. After a fermentation period of 1 h, the culture is induced with IPTG (0.15 mM). 18.5 g of rhamnose feed solution are then added. After the initially introduced quantity of glycerol has been consumed, glycerol is then fed in continuously. After a fermentation period of 44 h, cell suspensions of 50 g DBM/l and 50 to 60 ku/l are obtained. The cells are cooled down to 4° C.

Example 2

Activity Test

50 µl of cell suspension are pipetted into 880 µl of sodium potassium phosphate buffer (10 mM) and the whole is equilibrated at 30° C. The reaction is started by adding 20 µl of methanolic mandelonitrile solution (12%). After 10 min, the enzyme reaction is stopped by adding 50 µl of 1M HC. The cell mass is centrifuged off and the concentration of mandelic acid in the supernatant is measured by means of HPLC (ODS Hypersil 100*2.0 mm, mobile phase: 75% H3PO4 (14.8 mM)/25% methanol; flow rate: 0.5 ml/min; injection volume: 2 µl; column temperature: 40° C.; detection: 210 nm; mandelic acid retention time: 0.9 min).

Example 3

Storing with Benzaldehyde 14 h after the end of the fermentation, the cell suspension was adjusted to a pH of 6.0, 6.6 or 7.2 with NaOH or H$_2$SO$_4$ and then treated with benzaldehyde. The samples were stored at 4° C. or 22° C. Enzyme activity was determined at 0.6, 3.6 and 6.6 days after the end of the fermentation.
Storage at 22° C.:

| | | Storage period | | |
|---|---|---|---|---|
| | | 0.6 d | 3.6 d | 6.6 d |
| | pH | Activity in kU/l | | |
| Without addition | 7.2 | 51.0 | 49.0 | 48.7 |
| 1 mM benzaldehyde | 7.2 | 55.8 | 50.4 | 48.7 |
| 5 mM benzaldehyde | 7.2 | 47.1 | 51.7 | 52.9 |
| 10 mM benzaldeyde | 7.2 | 53.8 | 52.7 | 51.3 |
| Without addition | 6.6 | 51.5 | 50.5 | 50.9 |
| 1 mM benzaldehyde | 6.6 | 53.2 | 53.0 | 53.1 |
| 5 mM benzaldehyde | 6.6 | 47.1 | 54.3 | 58.0 |
| 10 mM benzaldeyde | 6.6 | 51.3 | 49.4 | 55.4 |
| Without addition | 6.0 | 54.8 | 45.6 | 44.5 |
| 1 mM benzaldehyde | 6.0 | 55.1 | 50.6 | 51.0 |
| 5 mM benzaldehyde | 6.0 | 51.8 | 51.5 | 54.9 |
| 10 mM benzaldeyde | 6.0 | 51.3 | 53.0 | 49.2 |

Storage at 4° C.:

|  | pH | Storage period | | |
|---|---|---|---|---|
|  |  | 0.6 d | 3.6 d | 6.6 d |
|  |  | Activity in kU/l | | |
| Without addition | 7.2 | 51.0 | 48.6 | 47.8 |
| 1 mM benzaldehyde | 7.2 | 55.8 | 46.8 | 47.5 |
| 5 mM benzaldehyde | 7.2 | 47.1 | 48.3 | 50.7 |
| 10 mM benzaldeyde | 7.2 | 53.8 | 51.2 | 49.2 |
| Without addition | 6.6 | 51.5 | 49.5 | 45.3 |
| 1 mM benzaldehyde | 6.6 | 53.2 | 52.3 | 52.5 |
| 5 mM benzaldehyde | 6.6 | 47.1 | 52.0 | 55.7 |
| 10 mM benzaldeyde | 6.6 | 51.3 | 55.5 | 51.9 |
| Without addition | 6.0 | 54.8 | 42.8 | 34.9 |
| 1 mM benzaldehyde | 6.0 | 55.1 | 49.9 | 48.3 |
| 5 mM benzaldehyde | 6.0 | 51.8 | 52.3 | 53.0 |
| 10 mM benzaldeyde | 6.0 | 51.3 | 51.5 | 50.2 |

Example 4

Storing with CBA 14 h after the end of the fermentation, the cell suspension was adjusted to a pH of 6.0, 6.6. or 7.2 with NaOH or $H_2SO_4$ and then treated with 2-chlorobenzaldehyde. The samples were stored at 4° C. or 22° C. The enzyme activity was determined at 0.6, 3.6 and 6.6 days after the end of the fermentation.

Storage at 22° C.:

|  | pH | Storage period | | |
|---|---|---|---|---|
|  |  | 0.6 d | 3.6 d | 6.6 d |
|  |  | Activity in kU/l | | |
| Without addition | 7.2 | 51.0 | 49.0 | 48.7 |
| 1 mM 2-chlorobenzaldehyde | 7.2 | 51.3 | 52.8 | 53.2 |
| 5 mM 2-chlorobenzaldehyde | 7.2 | 53.3 | 51.4 | 50.1 |
| 10 mM 2-chlorobenzaldehyde | 7.2 | 48.3 | 52.9 | 54.0 |
| Without addition | 6.6 | 51.5 | 50.5 | 50.9 |
| 1 mM 2-chlorobenzaldehyde | 6.6 | 48.8 | 55.0 | 57.2 |
| 5 mM 2-chlorobenzaldehyde | 6.6 | 50.6 | 56.7 | 55.5 |
| 10 mM 2-chlorobenzaldehyde | 6.6 | 47.4 | 56.2 | 58.6 |
| Without addition | 6.0 | 54.8 | 45.6 | 44.5 |
| 1 mM 2-chlorobenzaldehyde | 6.0 | 52.4 | 53.8 | 54.5 |
| 5 mM 2-chlorobenzaldehyde | 6.0 | 52.5 | 55.0 | 59.1 |
| 10 mM 2-chlorobenzaldehyde | 6.0 | 53.5 | 55.7 | 52.4 |

Storage at 4° C.:

|  | pH | Storage period | | |
|---|---|---|---|---|
|  |  | 0.6 d | 3.6 d | 6.6 d |
|  |  | Activity in kU/l | | |
| Without addition | 7.2 | 51.0 | 48.6 | 47.8 |
| 1 mM 2-chlorobenzaldehyde | 7.2 | 51.3 | 48.3 | 45.2 |
| 5 mM 2-chlorobenzaldehyde | 7.2 | 53.3 | 51.2 | 48.1 |
| 10 mM 2-chlorobenzaldehyde | 7.2 | 48.3 | 51.0 | 49.9 |
| Without addition | 6.6 | 51.5 | 49.5 | 45.3 |
| 1 mM 2-chlorobenzaldehyde | 6.6 | 48.8 | 55.1 | 54.7 |
| 5 mM 2-chlorobenzaldehyde | 6.6 | 50.6 | 56.3 | 53.6 |
| 10 mM 2-chlorobenzaldehyde | 6.6 | 47.4 | 55.0 | 58.5 |
| Without addition | 6.0 | 54.8 | 42.8 | 34.9 |
| 1 mM 2-chlorobenzaldehyde | 6.0 | 52.4 | 53.5 | 56.9 |
| 5 mM 2-chlorobenzaldehyde | 6.0 | 52.5 | 55.6 | 53.8 |
| 10 mM 2-chlorobenzaldehyde | 6.0 | 53.5 | 55.7 | 47.6 |

Example 5

Long-Term Storage

Figure 2:
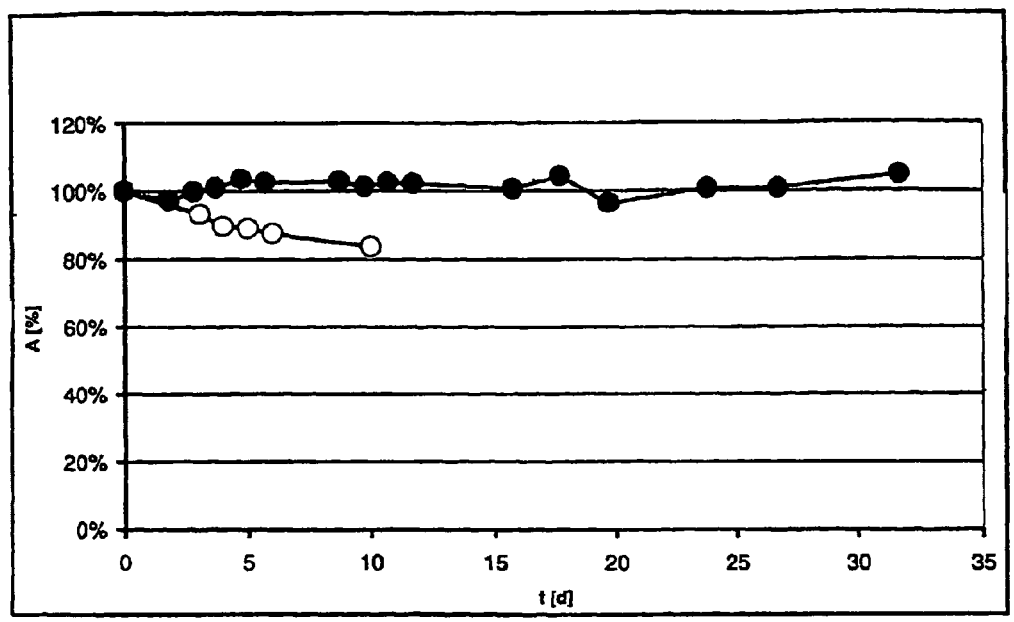
FIG. 2: Storage stability of a nitrilase for producing (R)-mandelic acid. The figure depicts the decrease in the activity (A; in % of the initial activity) of preparations of an $E.$ $coli$-expressed nitrilase without added 2-chlorobenzaldehyde (open circles) as compared with an otherwise identical preparation containing added 2-chlorobenzaldehyde (closed circles). The figure depicts a period (t) of up to 32 days (d).

The cell suspension was adjusted to pH 6.6 after which 2-chlorobenzaldehyde was added to a concentration of 1.35 mM and the cell suspension was stored at 4° C. The course of the activity is depicted in FIG. 2.

---

We claim:

1. A method for preserving and/or storing a microorganism which exhibits at least one nitrilase enzyme activity, comprising preserving and/or storing the microorganism in an aqueous medium which comprises at least one aldehyde selected from the group consisting of benzaldehyde and chlorobenzaldehyde in a total aldehyde concentration of from 1.0 to 10 mM at a pH of 6.0 to 7.2, wherein the aqueous medium comprises a total concentration of cyanide compounds selected from the group consisting of nitriles, hydrocyanic acid and cyanide salts of no more than 10 mol % of the total aldehyde concentration.

2. The method of claim 1, wherein the preservation step is carried out before the microorganism is treated with a reactant whose reaction is to be catalyzed by the microorgansim.

3. The method of claim 1, wherein the microorganism is selected from the species of the Enterobacteriaceae or Nocardiaceae family.

4. The method of claim 1, wherein the microorganism is selected from the group consisting of *Pseudomonas, Burkholderia, Nocardia, Acetobacter, Gluconobacter, Corynebacterium, Brevibacterium, Bacillus, Clostridium, Cyanobacter, Staphylococcus, Aerobacter, Alcaligenes, Rhodococcus* and *Penicillium*.

5. The method of claim 1, further comprising adding into the aqueous medium
   a) at least one inorganic salt at a concentration of at least 100 mM; or
   b) amides.

6. The method of claim 1, wherein the at least one nitrilase enzyme activity in said microorganism is preserved for a period of up to 37 days.

7. The method of claim 1, wherein the preserving and/or storing is at 0° C. to 22° C.

8. The method of claim 1, wherein the at least one aldehyde is chlorobenzaldehyde.

9. The method of claim 1, wherein said microorganism is of recombinant origin.

10. A method for preserving and/or storing a microorganism which exhibits at least one nitrilase enzyme activity, comprising:
    (a) preserving and/or storing the microorganism in an aqueous medium which comprises at least one aldehyde selected from the group consisting of benzaldehyde and chlorobenzaldehyde in a total aldehyde concentration of from 1.0 to 10 mM at a pH of 6.0 to 7.2,
    wherein the aqueous medium comprises a total concentration of cyanide compounds selected from the group consisting of nitriles, hydrocyanic acid and cyanide salts of no more than 10 mol % of the total aldehyde concentration, and
    (b) adding at least one inorganic salt at a concentration of at least 100 mM.

11. The method of claim 10, wherein the at least one aldehyde is chlorobenzaldehyde.

12. The method of claim 10, wherein said microorganism is of recombinant origin.

13. The method of claim 10, wherein the microorganism is selected from the species of the Enterobacteriaceae or Nocardiaceae family.

14. The method of claim 10, wherein the microorganism is selected from the group consisting of *Pseudomonas, Burkholderia, Nocardia, Acetobacter, Gluconobacter, Corynebacterium, Brevibacterium, Bacillus, Clostridium, Cyanobacter, Staphylococcus, Aerobacter, Alcaligenes, Rhodococcus* and *Penicillium*.

15. A method for preserving and/or storing a microorganism which exhibits at least one nitrilase enzyme activity, comprising preserving and/or storing the microorganism in an aqueous medium which comprises at least one aldehyde selected from the group consisting of benzaldehyde and chlorobenzaldehyde in a total aldehyde concentration of from 1.0 to 10 mM at a pH of 6.0 to 7.2, wherein the aqueous medium does not comprise a cyanide compounds.

16. The method of claim 15, wherein the at least one aldehyde is chlorobenzaldehyde.

17. The method of claim 15, wherein said microorganism is of recombinant origin.

18. The method of claim 15, further comprising adding into the aqueous medium
    a) at least one inorganic salt at a concentration of at least 100 mM; or
    b) amides.

19. The method of claim 15, wherein the microorganism is selected from the species of the Enterobacteriaceae or Nocardiaceae family.

20. The method of claim 15, wherein the microorganism is selected from the group consisting of *Pseudomonas, Burkholderia, Nocardia, Acetobacter, Gluconobacter, Corynebacterium, Brevibacterium, Bacillus, Clostridium, Cyanobacter, Staphylococcus, Aerobacter, Alcaligenes, Rhodococcus* and *Penicillium*.

* * * * *

SEQUENCE LISTING

```
<160> NUMBER OF SEQ ID NOS: 2

<210> SEQ ID NO 1
<211> LENGTH: 1071
<212> TYPE: DNA
<213> ORGANISM: Alcaligenes faecalis
<220> FEATURE:
<221> NAME/KEY: CDS
<222> LOCATION: (1)..(1068)
<223> OTHER INFORMATION: coding for nitrilase

<400> SEQUENCE: 1 atg cag aca aga aaa atc gtc cgg gca gcc gcc gta cag gcc gcc tct        48
Met Gln Thr Arg Lys Ile Val Arg Ala Ala Ala Val Gln Ala Ala Ser
  1               5                  10                  15 ccc aac tac gat ctg gca acg ggt gtt gat aaa acc att gag ctg gct        96
Pro Asn Tyr Asp Leu Ala Thr Gly Val Asp Lys Thr Ile Glu Leu Ala
             20                  25                  30 cgt cag gcc cgc gat gag ggc tgt gac ctg atc gtg ttt ggt gaa acc       144
Arg Gln Ala Arg Asp Glu Gly Cys Asp Leu Ile Val Phe Gly Glu Thr
         35                  40                  45 tgg ctg ccc gga tat ccc ttc cac gtc tgg ctg ggc gca ccg gcc tgg       192
Trp Leu Pro Gly Tyr Pro Phe His Val Trp Leu Gly Ala Pro Ala Trp
```

-continued

```
            50                  55                  60
tcg ctg aaa tac agt gcc cgc tac tat gcc aac tcg ctc tcg ctg gac       240
Ser Leu Lys Tyr Ser Ala Arg Tyr Tyr Ala Asn Ser Leu Ser Leu Asp
 65              70                  75                  80 agt gca gag ttt caa cgc att gcc cag gcc gca cgg acc ttg ggt att       288
Ser Ala Glu Phe Gln Arg Ile Ala Gln Ala Ala Arg Thr Leu Gly Ile
                 85                  90                  95 ttc atc gca ctg ggt tat agc gag cgc agc ggc ggc agc ctt tac ctg       336
Phe Ile Ala Leu Gly Tyr Ser Glu Arg Ser Gly Gly Ser Leu Tyr Leu
            100                 105                 110 ggc caa tgc ctg atc gac gac aag ggc gag atg ctg tgg tcg cgt cgc       384
Gly Gln Cys Leu Ile Asp Asp Lys Gly Glu Met Leu Trp Ser Arg Arg
        115                 120                 125 aaa ctc aaa ccc acg cat gta gag cgc acc gta ttt ggt gaa ggt tat       432
Lys Leu Lys Pro Thr His Val Glu Arg Thr Val Phe Gly Glu Gly Tyr
    130                 135                 140 gcc cgt gat ctg att gtg tcc gac aca gaa ctg gga cgc gtc ggt gct       480
Ala Arg Asp Leu Ile Val Ser Asp Thr Glu Leu Gly Arg Val Gly Ala
145                 150                 155                 160 cta tgc tgc tgg gag cat ttg tcg ccc ttg agc aag tac gcg ctg tac       528
Leu Cys Cys Trp Glu His Leu Ser Pro Leu Ser Lys Tyr Ala Leu Tyr
                165                 170                 175 tcc cag cat gaa gcc att cac att gct gcc tgg ccg tcg ttt tcg cta       576
Ser Gln His Glu Ala Ile His Ile Ala Ala Trp Pro Ser Phe Ser Leu
            180                 185                 190 tac agc gaa cag gcc cac gcc ctc agt gcc aag gtg aac atg gct gcc       624
Tyr Ser Glu Gln Ala His Ala Leu Ser Ala Lys Val Asn Met Ala Ala
        195                 200                 205 tcg caa atc tat tcg gtt gaa ggc cag tgc ttt acc atc gcc gcc agc       672
Ser Gln Ile Tyr Ser Val Glu Gly Gln Cys Phe Thr Ile Ala Ala Ser
    210                 215                 220 agt gtg gtc acc caa gag acg cta gac atg ctg gaa gtg ggt gaa cac       720
Ser Val Val Thr Gln Glu Thr Leu Asp Met Leu Glu Val Gly Glu His
225                 230                 235                 240 aac gcc ccc ttg ctg aaa gtg ggc ggc ggc agt tcc atg att ttt gcg       768
Asn Ala Pro Leu Leu Lys Val Gly Gly Gly Ser Ser Met Ile Phe Ala
                245                 250                 255 ccg gac gga cgc aca ctg gct ccc tac ctg cct cac gat gcc gag ggc       816
Pro Asp Gly Arg Thr Leu Ala Pro Tyr Leu Pro His Asp Ala Glu Gly
            260                 265                 270 ttg atc att gcc gat ctg aat atg gag gag att gcc ttc gcc aaa gcg       864
Leu Ile Ile Ala Asp Leu Asn Met Glu Glu Ile Ala Phe Ala Lys Ala
        275                 280                 285 atc aat gac ccc gta ggc cac tat tcc aaa ccc gag gcc acc cgt ctg       912
Ile Asn Asp Pro Val Gly His Tyr Ser Lys Pro Glu Ala Thr Arg Leu
    290                 295                 300 gtg ctg gac ttg ggg cac cga gac ccc atg act cgg gtg cac tcc aaa       960
Val Leu Asp Leu Gly His Arg Asp Pro Met Thr Arg Val His Ser Lys
305                 310                 315                 320 agc gtg acc agg gaa gag gct ccc gag caa ggt gtg caa agc aag att      1008
Ser Val Thr Arg Glu Glu Ala Pro Glu Gln Gly Val Gln Ser Lys Ile
                325                 330                 335 gcc tca gtc gct atc agc cat cca cag gac tcg gac aca ctg cta gtg      1056
Ala Ser Val Ala Ile Ser His Pro Gln Asp Ser Asp Thr Leu Leu Val
            340                 345                 350 caa gag ccg tct tga                                                  1071
Gln Glu Pro Ser
        355
```

```
<210> SEQ ID NO 2
<211> LENGTH: 356
<212> TYPE: PRT
<213> ORGANISM: Alcaligenes faecalis

<400> SEQUENCE: 2

Met Gln Thr Arg Lys Ile Val Arg Ala Ala Val Gln Ala Ala Ser
 1               5                  10                  15

Pro Asn Tyr Asp Leu Ala Thr Gly Val Asp Lys Thr Ile Glu Leu Ala
                 20                  25                  30

Arg Gln Ala Arg Asp Glu Gly Cys Asp Leu Ile Val Phe Gly Glu Thr
             35                  40                  45

Trp Leu Pro Gly Tyr Pro Phe His Val Trp Leu Gly Ala Pro Ala Trp
 50                  55                  60

Ser Leu Lys Tyr Ser Ala Arg Tyr Tyr Ala Asn Ser Leu Ser Leu Asp
 65                  70                  75                  80

Ser Ala Glu Phe Gln Arg Ile Ala Gln Ala Ala Arg Thr Leu Gly Ile
                 85                  90                  95

Phe Ile Ala Leu Gly Tyr Ser Glu Arg Ser Gly Gly Ser Leu Tyr Leu
                100                 105                 110

Gly Gln Cys Leu Ile Asp Asp Lys Gly Glu Met Leu Trp Ser Arg Arg
            115                 120                 125

Lys Leu Lys Pro Thr His Val Glu Arg Thr Val Phe Gly Glu Gly Tyr
130                 135                 140

Ala Arg Asp Leu Ile Val Ser Asp Thr Glu Leu Gly Arg Val Gly Ala
145                 150                 155                 160

Leu Cys Cys Trp Glu His Leu Ser Pro Leu Ser Lys Tyr Ala Leu Tyr
                165                 170                 175

Ser Gln His Glu Ala Ile His Ile Ala Ala Trp Pro Ser Phe Ser Leu
            180                 185                 190

Tyr Ser Glu Gln Ala His Ala Leu Ser Ala Lys Val Asn Met Ala Ala
        195                 200                 205

Ser Gln Ile Tyr Ser Val Glu Gly Gln Cys Phe Thr Ile Ala Ala Ser
    210                 215                 220

Ser Val Val Thr Gln Glu Thr Leu Asp Met Leu Glu Val Gly Glu His
225                 230                 235                 240

Asn Ala Pro Leu Leu Lys Val Gly Gly Gly Ser Ser Met Ile Phe Ala
                245                 250                 255

Pro Asp Gly Arg Thr Leu Ala Pro Tyr Leu Pro His Ala Glu Gly
            260                 265                 270

Leu Ile Ile Ala Asp Leu Asn Met Glu Glu Ile Ala Phe Ala Lys Ala
        275                 280                 285

Ile Asn Asp Pro Val Gly His Tyr Ser Lys Pro Glu Ala Thr Arg Leu
    290                 295                 300

Val Leu Asp Leu Gly His Arg Asp Pro Met Thr Arg Val His Ser Lys
305                 310                 315                 320

Ser Val Thr Arg Glu Glu Ala Pro Glu Gln Gly Val Gln Ser Lys Ile
                325                 330                 335

Ala Ser Val Ala Ile Ser His Pro Gln Asp Ser Asp Thr Leu Leu Val
            340                 345                 350

Gln Glu Pro Ser
        355
```